United States Patent
Ren et al.

(10) Patent No.: US 8,622,615 B2
(45) Date of Patent: Jan. 7, 2014

(54) CALIBRATION DEVICE FOR LOCATION OF CT X-RAY GENERATOR AND DETECTOR, CALIBRATION METHOD USING THE CALIBRATION DEVICE, AND CALIBRATION METHOD FOR CT SYSTEM

(75) Inventors: Jingyi Ren, Beijing (CN); Shuqin Dong, Beijiing (CN); Jiaqin Dong, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 335 days.

(21) Appl. No.: 13/182,570

(22) Filed: Jul. 14, 2011

(65) Prior Publication Data
US 2012/0012742 A1    Jan. 19, 2012

(30) Foreign Application Priority Data
Jul. 16, 2010  (CN) .......................... 2010 1 0232390

(51) Int. Cl.
*A61B 6/08*     (2006.01)
*G01D 18/00*    (2006.01)

(52) U.S. Cl.
USPC ............................ 378/207; 378/205; 378/901

(58) Field of Classification Search
USPC ............. 378/4–20, 91, 95, 98, 162–164, 204, 378/205, 207, 210, 901
See application file for complete search history.

(56) References Cited

U.S. PATENT DOCUMENTS

| 5,663,566 A * | 9/1997 | Maniawski et al. ........... 250/369 |
| 7,916,831 B2 | 3/2011 | Sun et al. |
| 2010/0142669 A1 | 6/2010 | Ren et al. |

OTHER PUBLICATIONS

Toth et al.,"A dose reduction x-ray beam positioning system for high-speed multislice CT scanners", Med. Phys., Dec. 2000, pp. 2659-2668, 27(12).

* cited by examiner

*Primary Examiner* — Anastasia Midkiff
(74) *Attorney, Agent, or Firm* — Armstrong Teasdale LLP (57) ABSTRACT

A calibration device for location of a CT X-ray generator and detector includes a splitting window, a splitting window bracket configured to support the splitting window, an integral bracket, and a spring including a first end connected to the splitting window bracket and a second end connected to the integral bracket.

20 Claims, 12 Drawing Sheets

CALIBRATION DEVICE FOR LOCATION OF CT X-RAY GENERATOR AND DETECTOR, CALIBRATION METHOD USING THE CALIBRATION DEVICE, AND CALIBRATION METHOD FOR CT SYSTEM

CROSS REFERENCE TO RELATED APPLICATIONS

This application claims the benefit of Chinese Patent Application No. 201010232390.7 filed Jul. 16, 2010, which is hereby incorporated by reference in its entirety.

BACKGROUND OF THE INVENTION

The embodiments described herein generally relate to a CT system, and in particular to a calibration device and method and calibration method for CT system.

At present, a known CT system widely applied to the medical field can image individual parts of a patient so as to assist medical workers in diagnosis and treatment of diseases.

When the CT system is used, two critical steps should be carried out—aligning a tube with a collimator on a scan plane and aligning the tube, the collimator, and a detector on the scan plane. These two steps can also be called POR (Plane of Rotation) and BOW (BEAM on Window) alignments. The POR is used to put an x-ray beam parallel to the plane of rotation. This ensures that a focal spot of the tube is aligned with the center of the collimator by moving the tube in a Z-direction. BOW is used to put the x-ray beam at the center of the detector on a Z-axis after the POR by adjusting the detector in the Z-direction. The idea is to treat the focal spot of the tube and the collimator as a reference plane and enable the center of the detector to be coplanar with said reference plane.

Figure 1:
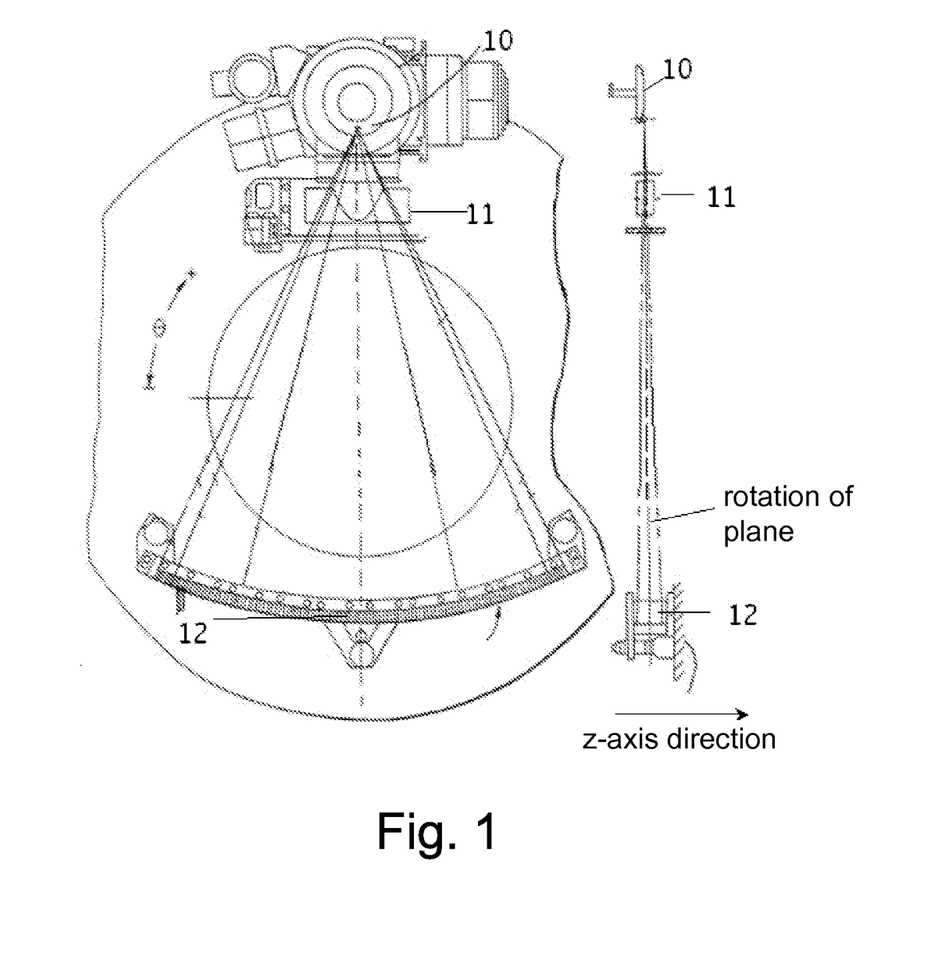
FIG. 1 is a simple structural diagram of a CT system.

FIG. 1 is a diagram of a single-slice CT system. As illustrated in FIG. 1, the CT system includes a tube 10, a collimator 11 and a detector 12. The plane of rotation refers to the plane on which the center of the tube 10, the center of the collimator 11, and the center of the detector 12 are aligned, and the z-axis direction refers to the direction perpendicular to the plane of rotation.

Currently, as for the POR, films are placed at the bottom of an aperture of a back cover of the CT system. The films are exposed twice respectively at 0 degree and 180 degrees of the x-ray tube. The difference of the x-ray profiles obtained by exposing the films twice is the amount of misalignment. The amount of misalignment is measured with a ruler or a micrometer. Then, according to the obtained amount of misalignment, the tube is adjusted so that the difference of the x-ray profiles obtained by two exposures is substantially 0, indicating that the POR has been aligned.

As for the BOW, three films are respectively placed on the left side, the center and the right side of channels of the detector. Then, these three films are exposed and checked to obtain the amount of misalignment in the three positions. Adjustment is then performed so that said amount of misalignment is substantially 0, i.e. it indicates that the BOW has been aligned.

The aforesaid technique is simple, effective and easy to be understood. However, the technique has following defects.

Firstly, because the aforesaid method needs to use films, but the films are one-off, generally speaking, at least 8 films are needed totally for the POR and BOW, wherein 4 films are used before alignment and another 4 films are used after alignment for double check. If the double check fails, more films may be needed. Therefore, the cost is high according to the prior technical method.

Secondly, because of use of the film, it is not good to environment.

Thirdly, because the amount of misalignment is measured with a ruler or a micrometer according to the prior technique, but the profile edge on the film is usually unclear in fact, the obtained result is not accurate.

SUMMARY OF THE INVENTION

The embodiments described herein provide a calibration device and method with a low cost and a calibration method for CT system.

The calibration device for location of CT x-ray generator and detector described herein includes a splitting window, a splitting window bracket, an integral bracket, and a spring. The splitting window bracket is used to support the splitting window. One end of the spring is connected to the splitting window bracket, and the other end is connected to the integral bracket.

Preferably, two windows are opened at the two parts at the opposite angles in the four parts of the splitting window divided by the two center lines of the splitting window.

Preferably, the calibration device for location of CT x-ray generator and detector include a bolt for adjusting the splitting window.

In another aspect, a calibration method using the aforesaid calibration device is used to calibrate the location of a CT x-ray generator and detector. The method includes placing the calibration device in a first position on the scan plane, exposing the calibration device respectively at 0 degree and at 180 degree by the CT x-ray generator, obtaining the offset of the tube based on the triangle relationship among an x-ray profile projected on the detector, the tube, and the ISO center, and adjusting the tube based on the offset of the tube to position the focal spot of the tube and the center of the collimator onto the scan plane.

Preferably, the calibration method further includes placing the calibration devices on the left side, the center, and the right side of the channels of the detector; then, exposing the three calibration devices; acquiring datum after exposure obtained by the detector; calculating the amount of misalignment at these three places based on the obtained data; and adjusting the detector to enable the amount of misalignment to be substantially 0.

Preferably, obtaining the offset of the tube based on the triangle relationship projected on the detector among an x-ray profile, the tube, and the ISO center includes calculating displacement a of the center of the calibration device on the detector when the calibration device is moved from a first position to a second position. The offset ?? of the tube is obtained according to the following formula:

$$?? = \frac{a \times C \times E}{A \times D}$$

wherein,
C represents a distance from the focal spot of an x-ray tube 10 to the second position; E represents a distance from the focal spot of an x-ray tube 10 to an aperture of a collimator 11; A represents a distance from the focal spot of an x-ray tube 10 to a detector 12; and D represents a distance from the first position to the second position.

Preferably, when the calibration device is moved from the first position to the second position, the displacement a of its center on the detector is obtained according to the following formula:

$$a = \frac{(T \times A)(1 + \gamma)}{2(1 - \gamma)} X$$

wherein, $$X = \frac{P_A - P_B}{P_A + P_B}$$

γ represents a ratio of the calibration device to an air projection; T is an x-ray thickness at the center of rotation; N is a distance from the focal spot of the tube to the ISO center; $P_A$ represents an average projection data in A Window; and $P_B$ represents an average projection data in B Window.

In yet another, the calibration method includes calibrating the plane of rotation; calibrating a beam on the window; aligning the detector with the focal spot of the tube when the tube is cool; aligning the collimator with the detector in the x-direction; calibrating the collimator in the z-direction; re-performing all the aforesaid steps in sequence based on the offset in the z-direction of the focal spot of the tube obtained in calibrating the collimator in the z-direction until the offset approximates to 0.

Preferably, calibrating the plane of rotation includes placing the calibration device in the first position on the scan plane; obtaining the offset of the tube based on the triangle relationship among an x-ray profile projected on the detector, the tube, and the ISO center; and adjusting the tube to position the focal spot of the tube and the center of the collimator onto the scan plane based on the offset of the tube.

Preferably, calibrating the beam on the window further includes placing the calibration devices on the left side, the center, and the right side of the channels of the detector; then, exposing the three calibration devices; acquiring datum after exposure obtained by the detector; calculating the amount of misalignment at these three places based on the obtained data; and adjusting the detector to enable the amount of misalignment to be substantially 0.

Preferably, obtaining the offset of the tube based on the triangle relationship among an x-ray profile projected on the detector, the tube, and the ISO center further includes calculating displacement a of the center of the calibration device on the detector when the calibration device is moved from the first position to the second position. The offset ?? of the tube is obtained according to the following formula:

$$?? = \frac{a \times C \times E}{A \times D}$$

wherein, C represents a distance from the focal spot of an x-ray tube 10 to the second position; E represents a distance from the focal spot of an x-ray tube 10 to an aperture of a collimator 11; A represents a distance from the focal spot of an x-ray tube 10 to a detector 12; D represents a distance from the first position to the second position.

Preferably, when the calibration device is moved from the first position to the second position, the displacement a of its center on the detector is obtained according to the following formula:

$$a = \frac{(T \times A)(1 + \gamma)}{2(1 - \gamma)} X$$

wherein, $$X = \frac{P_A - P_B}{P_A + P_B}$$

γ represents a ratio of the calibration device to an air projection; T is an x-ray thickness at the center of rotation; N is a distance from the focal spot of the tube to the ISO center; $P_A$ represents an average projection data in A window; and $P_B$ represents an average projection data in B window.

In comparison with the prior art, the advantages of the herein-described calibration device for location of CT system generator and detector, calibration method using the calibration device and calibration method for CT system are as follows.

First, the calibration device described herein can be repeatedly used without films so that the cost is saved.

Second, since the film is not used, it is good to the environment.

Third, since the embodiments described herein do not need the ruler or the micrometer to measure the amount of misalignment, the obtained result is accurate.

BRIEF DESCRIPTION OF THE DRAWINGS

In order to make more thoroughly understanding of the present disclosure, reference is made to the following descriptions in conjunction with the figures, in the drawings.

DETAILED DESCRIPTION OF THE INVENTION

Below embodiments of the present invention will be described in detail, but the present invention is not limited to the following embodiments.

Figure 2:
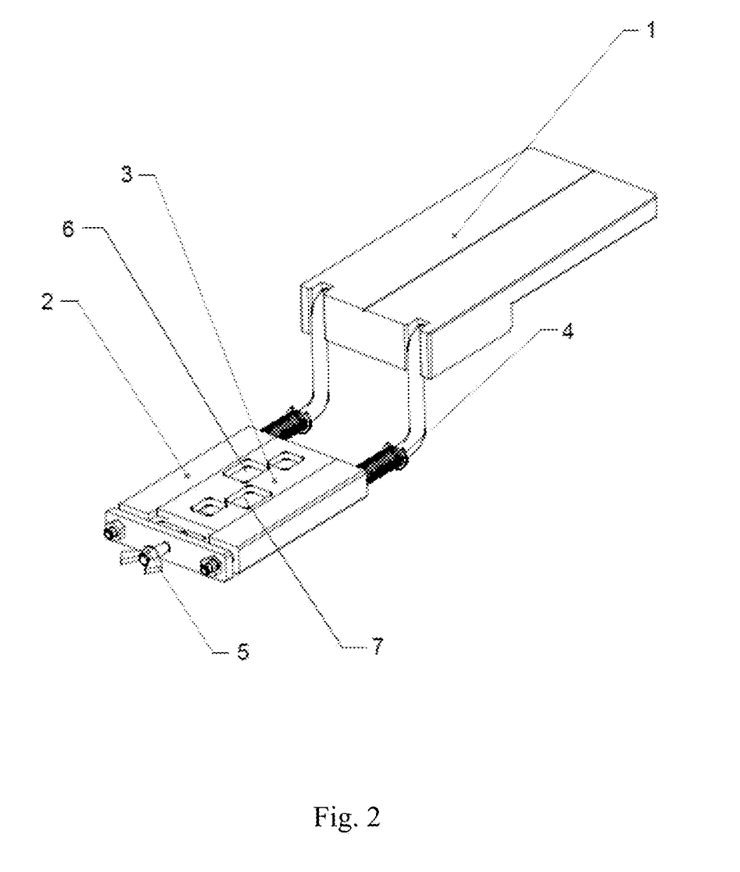
FIG. 2 is a structural diagram according to a calibration device for location of a CT x-ray generator and detector.

As shown in FIG. 2, a calibration device for location of a CT x-ray generator and detector includes a splitting window 3, a splitting window bracket 2, an integral bracket 1, and a spring 4. The splitting window bracket 2 is used to support the splitting window 3. A first end of the spring 4 is connected to the splitting window bracket 2, and a second end of the spring 4 is connected to the integral bracket 1. The splitting window 3 may be used to distinguish the position of the x-ray on a detector 12. The integral bracket 1 is used to fix the whole calibration device on a scan gantry 13. The spring 4 is used to adjust the position of the splitting window 3 relative to the detector 12.

Again as shown in FIG. 2, the calibration device further includes a bolt 5 for adjusting the splitting window 3. The bolt 5 can be combined with the spring 4 to adjust the position of the splitting window 3 relative to the detector 12.

Again as shown in FIG. 2, said calibration device further comprises a bolt 5 for adjusting the splitting window 3. The bolt 5 can be combined with the spring 4 to adjust the position of the said splitting window 3 relative to the detector 12.

The method using the calibration device for location of a CT x-ray generator and detector (hereinafter referred to as "jig") to perform a collimation will be described.

The jig is placed in some position between the center of rotation of the CT and the detector. The distance from the jig in this example to the center of rotation is 210 mm (millimeter).

Figure 3:
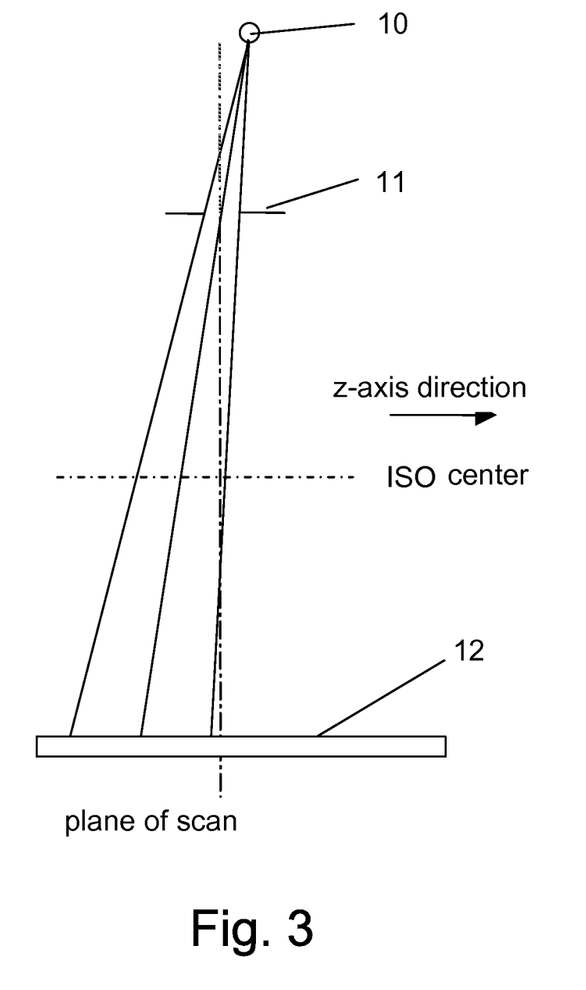
FIG. 3 is an x-ray profile under the state that the tube offsets.

FIG. 3 illustrates the usual relationship between an ISO center line and a scan plane after installation of a CT system. It can be seen that the focal spot of a tube 10 is not located on the theoretical scan plane. However, theoretically speaking, the focal spot of the tube 10, the center of collimator 11, and the center of the detector 12 should be on the scan plane.

First, a calibration of POR is made.

Figure 4:
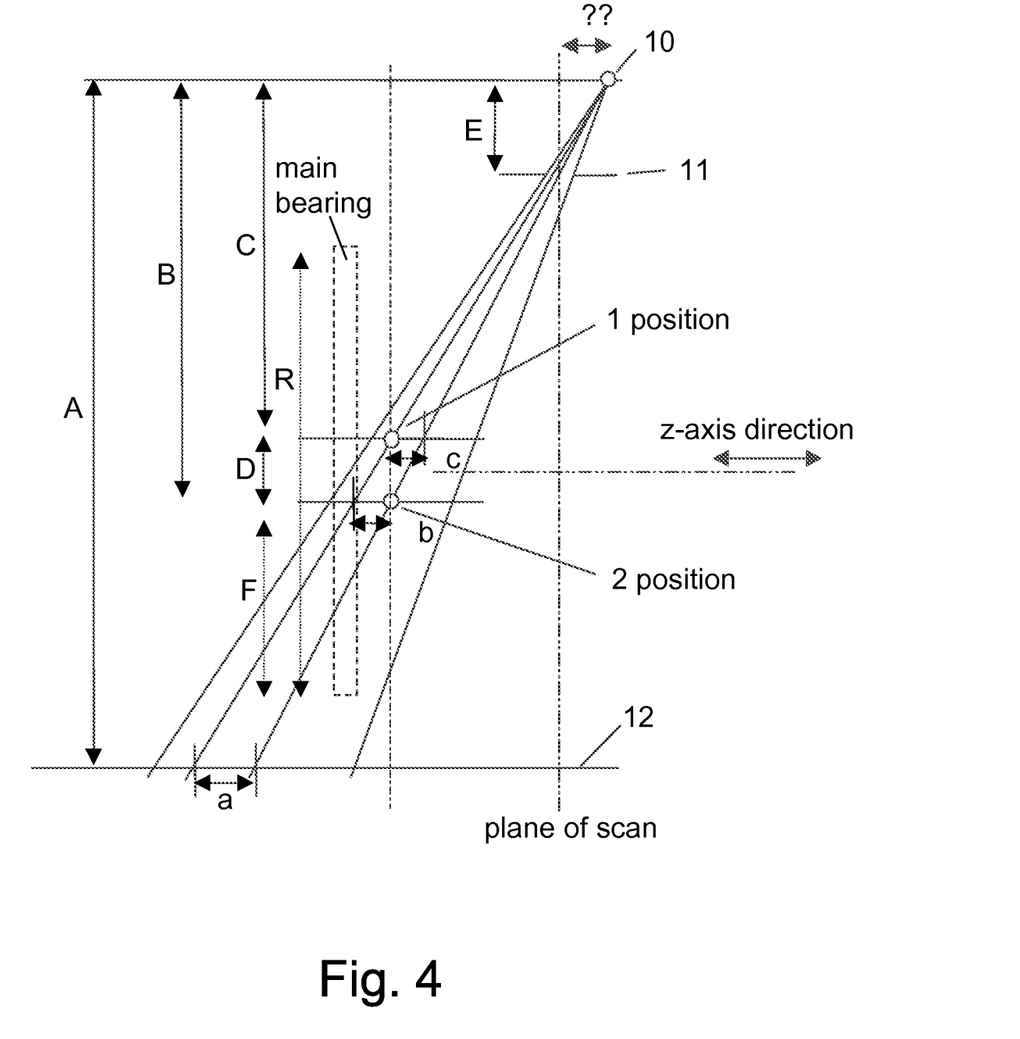
FIG. 4 is a diagram of adjusting a triangle relationship of the tube positions.

As shown in FIG. 4, it illustrates geometrical relationships in the z-direction represented by two scans that the tube 10 respectively transmits x-rays at 0 degree position and at 180 degree position to scan jig.

In the FIG. 4, C represents a distance from the focal spot of an x-ray tube 10 to a second position, 2 position; E represents a distance from the focal spot of an x-ray tube 10 to an aperture of a collimator 11; A represents a distance the focal spot of an x-ray tube 10 to a detector 12; D represents a distance from a first position, 1 position, to 2 position.

First, the jig is placed in the 1 position on the scan plane (at this time, the tube 10 is at 0 degree position). It is assumed that the center of the jig is projected on the detector 12, to scan the jig, the profile of the x-rays is obtained on the detector 12. Then, the jig is moved to the 2 position or the scan gantry 13 is rotated by 180 degrees, the jig is scanned. Another profile of the x-rays is obtained on the detector 12. If there is an offset from the focal spot of the x-ray tube 10 to the center of the collimator 11 or the scan plane (the offset is represented with "??"), projection of the jig on detector 12 moves a distance a ("a" represents the displacement projected from the center of the jig on the detector 12 when the jig is moved from 1 position to 2 position).

According to the geometrical relationship, it can be obtained:

$$\frac{??}{E} = \frac{c}{D} \tag{1}$$

$$\frac{c}{a} = \frac{C}{A} \tag{2}$$

According to equations (1) and (2), the following equation can be obtained:

$$?? = \frac{a \times C \times E}{A \times D} \tag{3}$$

As for the parameters in equation (3), according to a geometrical structure of a certain CT system, A, C, D and E are known and only parameter a is obtained by calculation.

Figure 5:
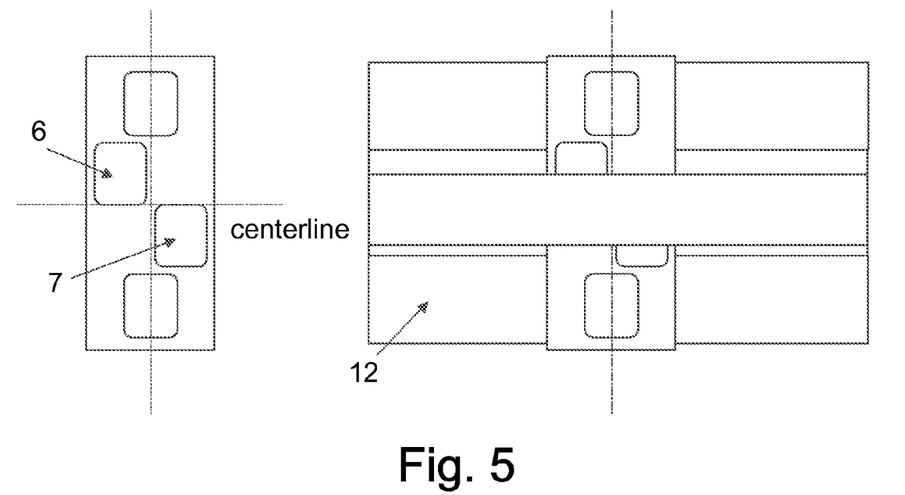
FIG. 5 is a schematical diagram of the location of the calibration device on the detector when the location of the detector is adjusted.

FIG. 5 illustrates the jig and the x-ray profile on the detector. According to FIG. 5, it can be seen that the x-ray profile in A window and the x-ray profile in B window are different if the centerline of the x-ray profile is not aligned with the centerline of the jig. The difference between x-ray profiles in A window and B window may be calculated through the original datum of the detector that are obtained when the tube 10 scans at 0 degree. The single-slice detector does not have a z-axis resolution. As such, A window and B window are respectively disposed on the two sides of the centerline of the jig and there is not any overlap regions along the centerline direction. The embodiments described herein use a x-ray resolution of the detector to solve a z-axis resolution.

Figure 6:
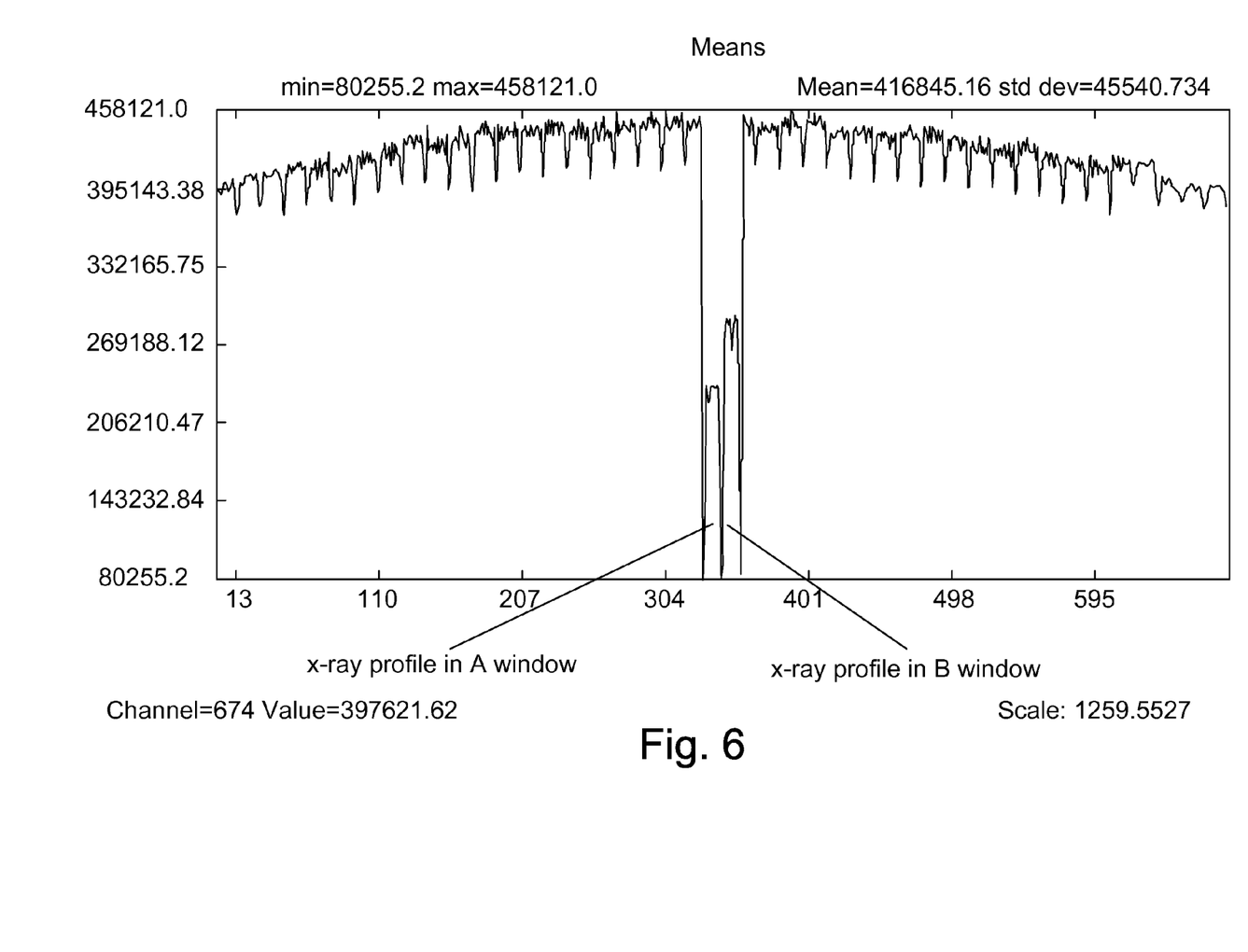
FIG. 6 is a profile of datum acquired by the detector under the state that the tube offsets.
Figure 7:
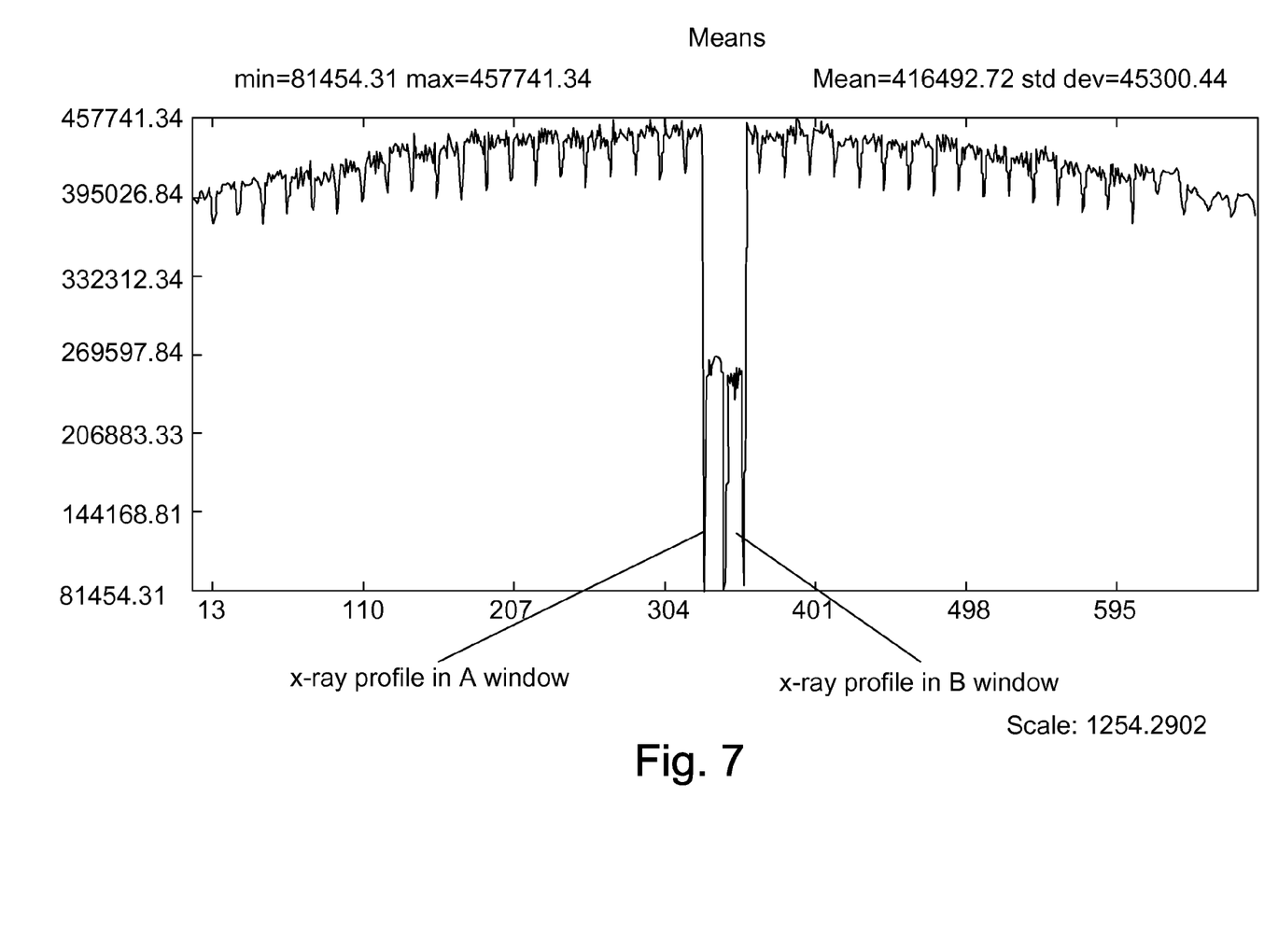
FIG. 7 is a profile of datum obtained by the detector under the state that the tube does not offset.
Figure 8:
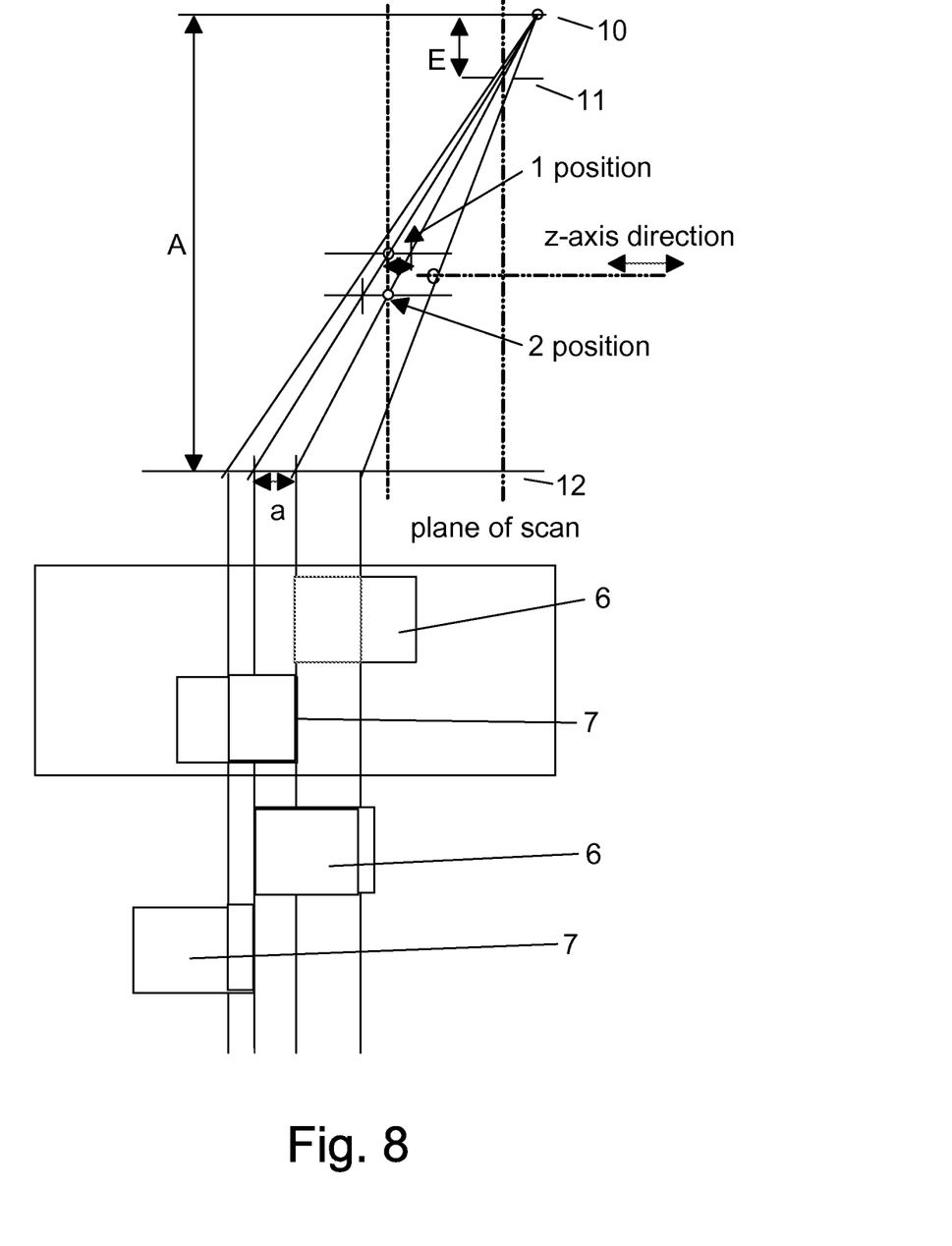
FIG. 8 is an x-ray profile of the calibration device under the state that the tube offsets.

FIG. 6 illustrates x-ray profiles obtained in A window and B window by the tube 10 transmitting x-rays on to the jig when the jig is at the 1 position. According to FIG. 6, it can be seen that the x-ray profile difference in the two windows is very great. Adjustment of a bolt 5 along the z-direction can make the x-ray profiles in A window and B window substantially identical as shown in FIG. 7. Then, the jig is moved to 2 position, or the scan gantry 13 is rotated by 180 degrees, so that x-ray profiles are obtained from A window and B window respectively. If the focal spot of the tube 10 has an offset relative to the center of the collimator 11 in the z-direction, at this time, the x-ray profiles in A window and B window have the difference as shown in FIG. 8.

In this embodiment, the unit of "a" is the millimeter. The x-ray profile obtained from the detector 12 is the average projection data. The average projection data relates to a projection area. Their relationship is described by the following equation. Because the widths of A window and B window are identical, an x-ray profile length can be used to replace its area. As shown in FIG. 8, AA is the length of the x-ray profile in A window and BB is the length of the x-ray profile in B window. It is assumed that $P_A$ represents the average projection data in A window and $P_B$ represents the average projection data in B window.

$$P_A = AA + \gamma BB$$

$$P_B = BB + \gamma AA \tag{4}$$

wherein, $\gamma$ is a ratio of the calibration device to an air projection, which is a constant.

Figure 9:
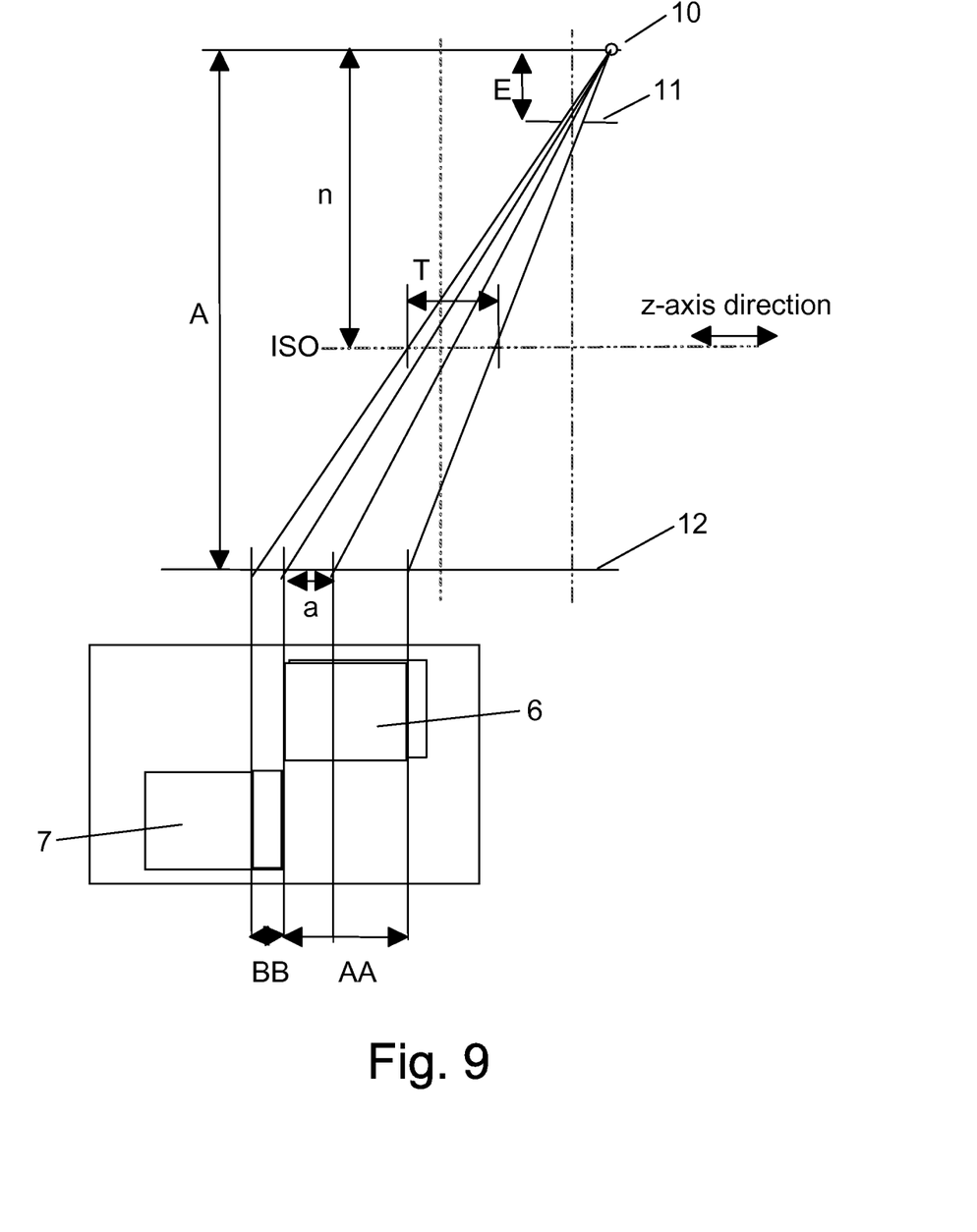
FIG. 9 is an x-ray profile of the calibration device under the state that the tube offsets.

According to FIG. 9, it can be known that $$2a = AA - BB \tag{5}$$

set:

$$X = \frac{P_A - P_B}{P_A + P_B} \quad (6)$$

therefore, $$a = \frac{(AA + BB)(1+\gamma)}{2(1-\gamma)} X \quad (7)$$

wherein, $$AA + BB = \frac{T \times A}{n} \quad (8)$$

where T is a thickness of x-rays at the center of rotation and n is a distance from the focal spot of the tube to ISO center.

Through the aforesaid calculation, "a" can be obtained and the offset of the tube can be obtained. According to the offset of the tube, the tube can be adjusted to the correct position so as to complete the calibration of POR.

Then, the calibration of BOW is made.

First, the calibration devices are placed on the left side, the center, and the right side of the channels of the detector. The three calibration devices are then exposed. Datum after exposure obtained by the detector are acquired, and the amount of misalignment at these three places are calculated according to the obtained datum. The detector is adjusted to enable the amount of misalignment to be substantially 0.

Theoretically, the calibration of BOW and the preceding calculation related to "a" are identical. The only difference is that the calibration of BOW is to directly place the jig on the detector 12. At this time, "a" is an offset of the centerline of the detector other than a projected displacement of the centerline.

The calibration is shown in the following embodiment.

First, the calibration device is placed at 210 mm away from the center of rotation. The tube exposes at 0 degree. At this time, according to the following equation (7), the offset "a" of the calibration device in the z-direction can be calculated.

$$a = \frac{(AA + BB)(1+\gamma)}{2(1-\gamma)} X \quad (7)$$

Then, the tube exposes at 180 degrees. At this time, according to equation (3), the offset of the tube at the z-direction can be calculated.

After adjustment of the tube 10 is completed, the position of the detector 12 is adjusted. Three calibration devices are directly placed on the left side, the center, and the right side of the detector 12 to expose by the tube at 0 degree.

As for datum obtained by the detector to which the calibration device on the left side corresponds, e.g.: PA=0.64492, and PB=0.78997, it can be according to the equation (6):

$$X = \frac{P_A - P_B}{P_A + P_B},$$

obtaining X=0.10109, which is introduced into the equation (7):

$$a = \frac{(AA + BB)(1+\gamma)}{2(1-\gamma)} X$$

obtaining a=8.5278 and X=0.8621 mm

For the datum obtained by the detector to which the calibration device on the right side corresponds, e.g.: $P_A$=0.46706, and $P_B$=0.59178, according to equation (6), X=0.11779 can be obtained. The value obtained for X is introduced into the equation (7) to obtain a=8.5278 and X=1.0044 mm.

For the datum obtained by the detector to which the calibration device in the middle corresponds, e.g.: $P_A$=0.66902, and $P_B$=0.78973, according to equation (6), X=0.08275 can be obtained. The value obtained for X is introduced into the equation (7) to obtain a=8.5278 and X=0.7056 mm.

After the aforesaid amount of misalignment is obtained, according to the amount of misalignment, the detector 12 can be aligned.

Figure 10:
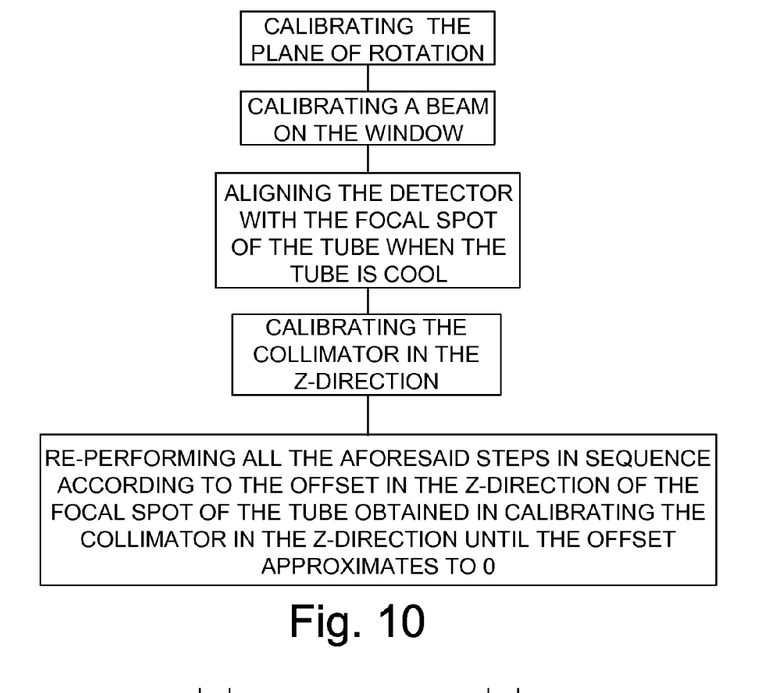
FIG. 10 is a schematical diagram of calibration method for a CT system.

In another aspect, calibration method for a CT system is provided. As shown in FIG. 10, the calibration method for the CT system includes calibrating the plane of rotation; calibrating a beam on the window; aligning the detector 12 with the focal spot of the tube when the tube 10 is cool; aligning the collimator 11 with the detector 12 in the x-direction; calibrating the collimator in the z-direction; and re-performing the aforesaid steps in sequence according to the offset in the z-direction of the focal spot of the tube obtained in calibrating the collimator in the z-direction until the offset approximates to 0.

The calibration of the plane of rotation is the calibration of the POR and the calibration of the beam on the window is the calibration of BOW. As for the calibration of POR and the calibration of BOW, any method that has been known or will be known by those skilled in the art can be used. After the calibration of POR and the calibration of BOW are performed on the CT system, the detector 12 and the focal spot of the tube are aligned when the tube 10 is cool. Next, the collimator 11 and the detector 12 are aligned in the x-direction. Then, the collimator is calibrated in the z-direction. Finally, the following steps are re-performed in sequence according to the offset in the z-direction of the focal spot of the tube obtained in the calibration of the collimator until the offset approximates to 0. More specifically, the following steps are re-preformed: calibrating the plane of rotation; calibrating a beam on the window; aligning the detector 12 with the focal spot of the tube when the tube 10 is cool; aligning the collimator 11 with the detector 12 in the x-direction; and calibrating the collimator in the z-direction. This can ensure more optimized calibration of POR and calibration of BOW and meanwhile, the better image quality can be achieved.

Calibrating the in the z-direction can refer to "A does reduction x-ray beam positioning system for high-speed multi-slice CT scanners" by Thomas L. Toth, Neil B. Bromberg, et al., December, 2000, American Association of Physicists in Medicine. The Toth et al. paper describes the process of calibrating the in detail. The following only simply introduces the method.

The calibration of the collimator includes performing a sweep scan during which a scan gantry is not rotated. During the sweep scan, datum are collected within the whole scope of the location of the collimator (as shown in FIGS. 11a, 11b and 11c).

Figure 11A:
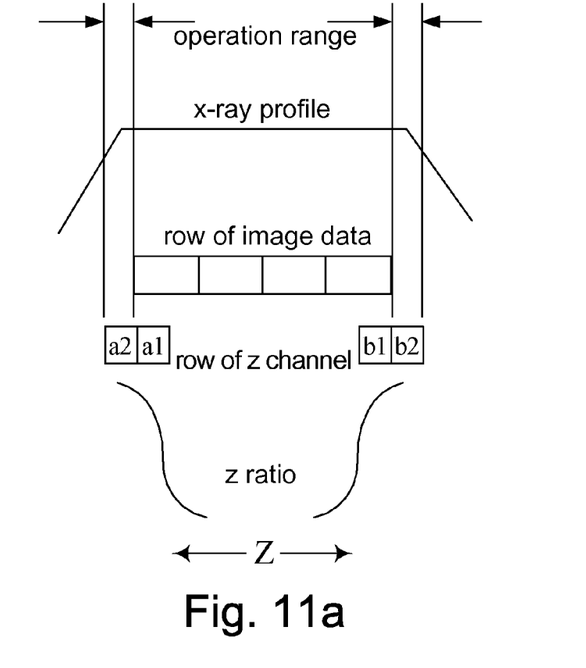
FIG. 11*a* is a schematical diagram of an x-ray intensity of the detector and signal amplitude of the detector.
Figure 11B:
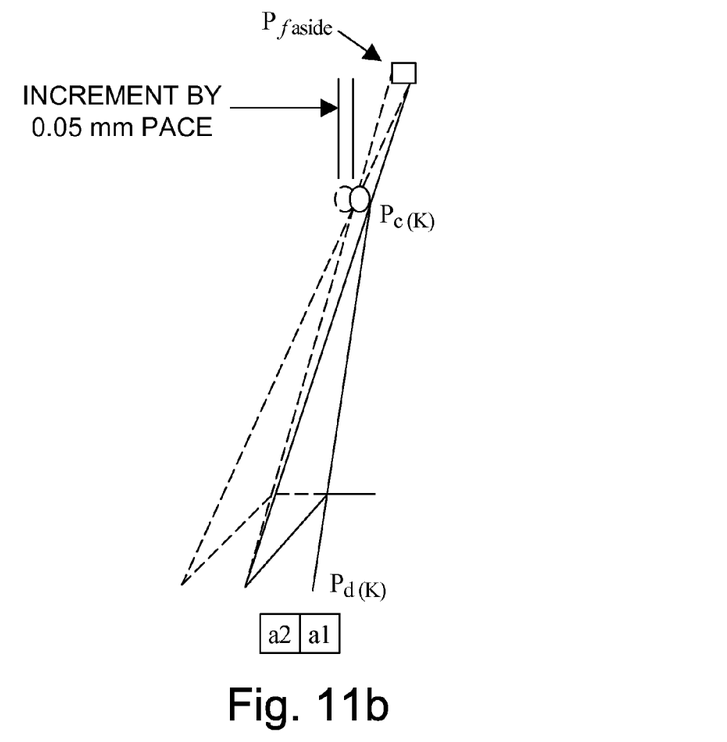
FIG. 11*b* is a schematical diagram of movement of a cam of the collimator along a z-direction.
Figure 11C:
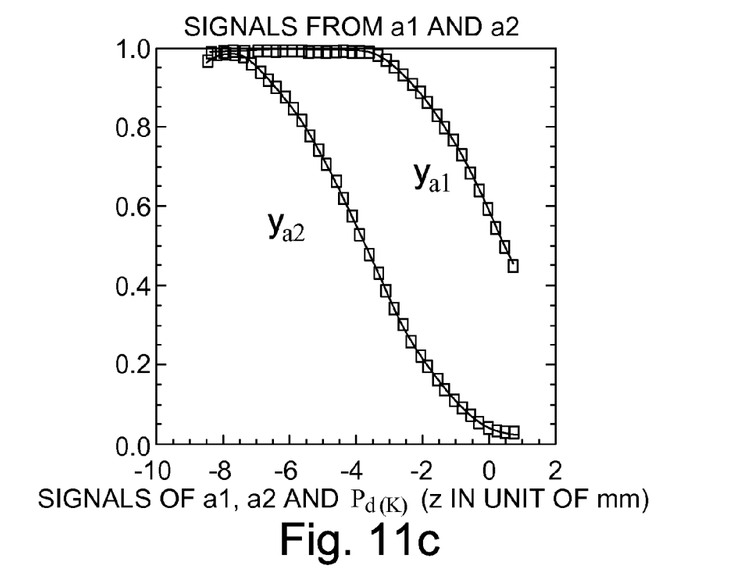
FIG. 11*c* is a diagram of the relationship between the amplitudes of signals measured by the detector unit and the position of the detector to which the cam corresponds.

FIG. 11a illustrates a schematic diagram of an x-ray intensity of the detector and amplitudes of the signals of the detector, wherein $y_{a1}$ and $y_{a2}$ represents amplitudes of x-ray signals detected by two detector units a1 and a2 on the A side of the detector, and $y_{b1}$ and $y_{b2}$ represents amplitudes of x-ray signals detected by two detector units b1 and b2 on the B side of the detector. In the following equations, $r_a$ represents an a signal ratio on an a-side and $r_b$ represents a ratio on a b-side. The following equations are met:

$$r_a = \frac{y_{a2}(z)}{y_{a1}(z)}$$

$$r_b = \frac{y_{b2}(z)}{y_{b1}(z)}$$

wherein, $y_{a2}(z)$ is the signal of the detector unit a2; $y_{a1}(z)$ is the signal of the detector unit a1; $y_{b2}(z)$ is the signal of detector unit b2; and $y_{b1}(z)$ is the signal of the detector unit b1.

FIG. 11b is a schematic diagram of movement of the cam of the collimator along a z-direction, wherein $P_c(K)$ is the position of the cam and $P_d(k)$ is the position of the detector to which the cam corresponds. $P_{f\,aside}$ represents the position of a focal spot on the a-side. a1 and a2 represent two detector units. The cam moves by 0.05 paces. K is a index of the position of the collimator.

FIG. 11c is a diagram of the relationship between the amplitude of a signal measured by the detector unit and the position of the detector to which the cam corresponds, wherein $y_{a1}$ and $y_{a2}$ respectively represents the amplitudes of x-ray signals detected by the two detector units a1 and a2.

Figure 11D:
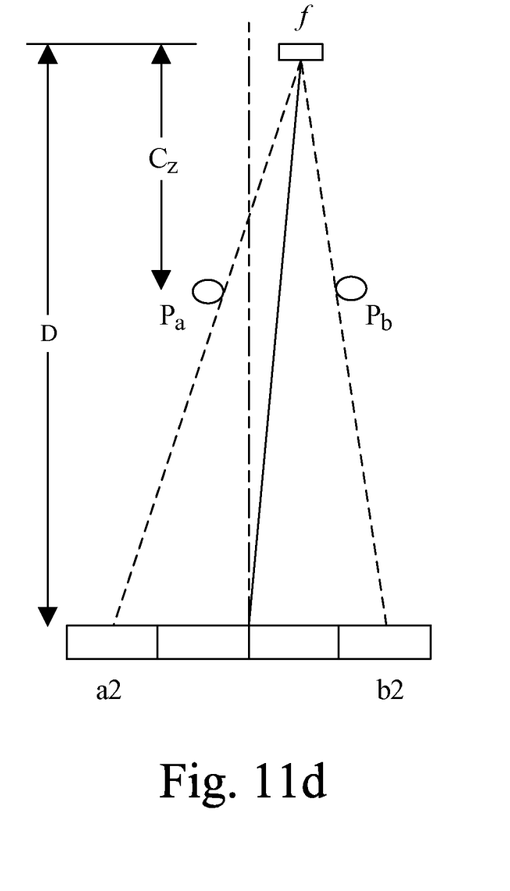
FIG. 11*d* illustrates a schematical diagram of determination of the focal spot of the tube.

FIG. 11d illustrates a schematical diagram of determination of the focal spot of the tube. The offset f of the focal spot of the tube in the z-direction can be obtained by the following equation:

$$f = \left(\frac{P_a + P_b}{2}\right)\left(\frac{D}{D - C_z}\right)$$

wherein, D is a distance from the focal spot to the detector; $C_z$ is a distance from the focal spot to the cam; $P_a$ represents the position of the cam when the signal of the detector unit a2 is a half of the full amplitude; $P_b$ represents the position of the cam when the signal of the detector unit b2 is a half of the full amplitude. After f is obtained, the previous steps of the calibration method for CT system are re-performed according to f until the value of f is in the vicinity of 0, e.g., f<0.02 mm, and the calibration is over.

Additionally, as for the calibration of the plane of rotation and the calibration of the beam on the window, the calibration method using the calibration device for location of the CT x-ray generator and detector can be used to perform the calibrations.

Calibrating the plane of rotation includes: placing the calibration device in a first position, 1 position, on the scan plane; exposing the calibration device respectively at 0 degree and at 180 degree using the CT x-ray generator; obtaining the offset of the tube based on the triangle relationship projected among an x-ray profile on the detector, the tube, and the ISO center; and adjusting the tube based on the offset of the tube to position the focal spot of the tube and the center of the collimator onto the scan plane.

Calibrating a beam on the window includes placing the calibration devices on the left side, the center, and the right side of the channels of the detector. The three calibration devices are then exposed, and datum after exposure obtained by the detector is acquired. The calibration further include calculating the amount of misalignment at these three places based on the obtained datum and adjusting the detector to enable the amount of misalignment to be substantially 0.

Obtaining the offset of the tube based on the triangle relationship projected on the detector among an x-ray profile, the tube, and the ISO center includes calculating displacement a of the center of the calibration device on the detector when the calibration device is moved from a first position (1 position) to a second position (2 position) and obtaining the offset ?? of the tube according to the following equation:

$$?? = \frac{a \times C \times E}{A \times D}$$

wherein,
C represents a distance from the focal spot of an x-ray tube 10 to 2 position; E represents a distance from the focal spot of an x-ray tube 10 to an aperture of a collimator 11; A represents a distance from the focal spot of an x-ray tube 10 to detector 12; and D represents a distance from 1 position to 2 position.

When the calibration device is moved from 1 position to 2 position, the displacement "a" of its center on the detector is obtained according to the following formula:

$$a = \frac{(T \times A)(1 + \gamma)}{2(1 - \gamma)} X$$

wherein, $$X = \frac{P_A - P_B}{P_A + P_B}$$

γ represents a ratio of the calibration device to an air projection; T is an x-ray thickness at the center of rotation; N is a distance from the focal spot of the tube to the ISO center; $P_A$ represents an average projection data in A Window; and $P_B$ represents an average projection data in B Window.

Because the calibration method using the calibration device for location of CT x-ray generator and detector has been described in the previous contents of this text in detail, they are not repeated here.

Although the embodiments of the present invention have been described above in combination of the drawings, those skilled in the art can change, amend or equivalently replace the present invention in various manners without departing from the concept and scope of the present invention. These changes, amendments and equivalent replacements are intended to fall within the concept and scope defined by the attached claims.

The invention claimed is:
1. A calibration device for location of a CT X-ray generator and detector, said calibration device comprising:
   a splitting window;
   a splitting window bracket configured to support the splitting window;

an integral bracket; and
a spring comprising a first end connected to the splitting window bracket and a second end connected to the integral bracket.

2. The calibration device according to claim 1, wherein the splitting window includes four parts divided by two center lines, two windows opened at two parts at opposite angles in the four parts.

3. The calibration device according to claim 1, further comprising a bolt configured to adjust the splitting window.

4. The calibration device according to claim 2, further comprising a bolt configured to adjust the splitting window.

5. A calibration method of using a calibration device to calibrate location for a CT X-ray generator and detector, the calibration device including a splitting window, a splitting window bracket configured to support the splitting window, an integral bracket, and a spring having a first end connected to the splitting window bracket and a second end connected to the integral bracket, said method comprising:
placing the calibration device in a first position on a scan plane;
exposing the calibration device at 0 degree and at 180 degree using the CT X-ray generator;
obtaining an offset of a tube based on a relationship among an x-ray profile projected on the detector, the tube, and an ISO center; and
adjusting the tube according to the offset to position a focal spot of the tube and a center of a collimator onto the scan plane.

6. The calibration method according to claim 5, further comprising:
placing one calibration device of a plurality of devices on each of a left side, a center, and a right side of channels of the detector;
exposing the plurality of calibration devices;
acquiring data after exposure obtained by the detector;
calculating an amount of misalignment at the left side, the center, and the right side based on the acquired data; and
adjusting the detector such that the amount of misalignment is substantially zero.

7. The calibration method according to claim 5, wherein obtaining an offset of a tube further comprises:
calculating a displacement a of a center of the calibration device on the detector when the calibration device is moved from the first position to a second position; and
obtaining an offset ?? of the tube using:

$$?? = \frac{a \times C \times E}{A \times D}$$

wherein C represents a distance from the focal spot of the tube to the second position; E represents a distance from the focal spot of the tube to an aperture of the collimator; A represents a distance from the focal spot of the tube to the detector; and D represents a distance from the first position to the second position.

8. The calibration method according to claim 6, wherein obtaining an offset of a tube further comprises:
calculating a displacement a of a center of the calibration device on the detector when the calibration device is moved from the first position to a second position; and
obtaining an offset ?? of the tube using:

$$?? = \frac{a \times C \times E}{A \times D}$$

wherein C represents a distance from the focal spot of the tube to the second position; E represents a distance from the focal spot of the tube to an aperture of the collimator; A represents a distance from the focal spot of the tube to the detector; and D represents a distance from the first position to the second position.

9. The calibration method according to claim 7, wherein obtaining a displacement a of a center of the calibration on the detector further comprises obtaining the displacement a when the calibration device is moved from the first position to the second position using:

$$a = \frac{(T \times A)(1 + \gamma)}{2(1 - \gamma)} X$$

wherein, $$X = \frac{P_A - P_B}{P_A + P_B}$$

where $\gamma$ represents a ratio of the calibration device to an air projection; T is an x-ray thickness at a center of rotation; $P_A$ represents an average projection data in an A Window; and $P_B$ represents an average projection data in a B Window.

10. The calibration method according to claim 8, displacement a of a center of the calibration on the detector further comprises obtaining the displacement a when the calibration device is moved from the first position to the second position using:

$$a = \frac{(T \times A)(1 + \gamma)}{2(1 - \gamma)} X$$

wherein, $$X = \frac{P_A - P_B}{P_A + P_B}$$

where $\gamma$ represents a ratio of the calibration device to an air projection; T is an x-ray thickness at a center of rotation; $P_A$ represents an average projection data in an A Window; and $P_B$ represents an average projection data in a B Window.

11. A calibration method for a CT system comprising:
calibrating a plane of rotation;
calibrating a beam on a window;
aligning a detector with a focal spot of a tube when the tube is cool;
aligning a collimator with the detector in an x-direction;
calibrating the collimator in a z-direction; and
re-performing the steps in sequence based on an offset in the z-direction of the focal spot obtained in calibrating the collimator in the z-direction until the offset approximates to zero.

12. The calibration method according to claim 11, wherein calibrating the plane of rotation further comprises:
  placing a calibration device in a first position on a scan plane;
  exposing the calibration device at 0 degree and at 180 degree using a CT x-ray generator;
  obtaining an offset of the tube based on a relationship among an x-ray profile projected on the detector, the tube, and an ISO center; and
  adjusting the tube based on the offset to position the focal spot and a center of the collimator onto the scan plane.

13. The calibration method according to claim 12, wherein calibrating a beam on a window comprises:
  placing one calibration device of a plurality of calibration devices on a left side, a center, and a right side of channels of the detector;
  exposing the plurality of calibration devices;
  acquiring data after exposure obtained by the detector;
  calculating an amount of misalignment at the left side, the center, and the right side based on the obtained data; and
  adjusting the detector such that the amount of misalignment is substantially zero.

14. The calibration method according to claim 13, wherein obtaining an offset of the tube further comprises:
  calculating a displacement a of a center of the calibration device on the detector when the calibration device is moved from the first position to a second position; and
  obtaining and offset ?? of the tube using:

$$?? = \frac{a \times C \times E}{A \times D}$$

wherein C represents a distance from the focal spot of the tube to the second position; E represents a distance from the focal spot of the tube to an aperture of the collimator; A represents a distance from the focal spot of the tube to the detector; and D represents a distance from the first position to the second position.

15. The calibration method according to claim 14, displacement a of a center of the calibration on the detector further comprises obtaining the displacement a when the calibration device is moved from the first position to the second position using:

$$a = \frac{(T \times A)(1 + \gamma)}{2(1 - \gamma)} X$$

wherein, $$X = \frac{P_A - P_B}{P_A + P_B}$$

where $\gamma$ represents a ratio of the calibration device to an air projection; T is an x-ray thickness at a center of rotation; $P_A$ represents an average projection data in an A Window; and $P_B$ represents an average projection data in a B Window.

16. The calibration method according to claim 11, wherein a calibration device includes a splitting window, calibrating a beam on a window further comprises calibrating the beam using the splitting window of the calibration device.

17. The calibration method according to claim 11, wherein a calibration device includes a splitting window, said method further comprising distinguishing a position of the beam on the detector using the splitting window of the calibration device.

18. The calibration method according to claim 12, wherein exposing the calibration device at 0 degree and at 180 degree further comprises:
  exposing the calibration device at 0 degree when the calibration device is located at the first position; and
  exposing the calibration device at 180 degree when the calibration device is located at a second position.

19. The calibration device according to claim 1, wherein the splitting window is configured to distinguish a position of a beam on the detector.

20. The calibration device according to claim 1, wherein the spring is configured to adjust a position of the splitting window with respect to the detector.

* * * * *